(12) United States Patent
Kuypers et al.

(10) Patent No.: US 11,285,281 B2
(45) Date of Patent: Mar. 29, 2022

(54) ELECTRICALLY OPERABLE RESUSCITATORS

(71) Applicants: Gilbert Jacobus Kuypers, Auckland (NZ); Richard Anthony McCulloch, Auckland (NZ)

(72) Inventors: Gilbert Jacobus Kuypers, Auckland (NZ); Richard Anthony McCulloch, Auckland (NZ)

(*) Notice: Subject to any disclaimer, the term of this patent is extended or adjusted under 35 U.S.C. 154(b) by 469 days.

(21) Appl. No.: 15/926,393

(22) Filed: Mar. 20, 2018

(65) Prior Publication Data

US 2019/0060592 A1 Feb. 28, 2019

Related U.S. Application Data

(63) Continuation of application No. 14/741,848, filed on Jun. 17, 2015, now abandoned, which is a (Continued)

(30) Foreign Application Priority Data

May 30, 2007 (NZ) ........................................ 555581

(51) Int. Cl.
*A61M 16/06* (2006.01)
*A61M 16/00* (2006.01)
(Continued)

(52) U.S. Cl.
CPC .... *A61M 16/0069* (2014.02); *A61M 16/0003* (2014.02); *A61M 16/0072* (2013.01); (Continued)

(58) Field of Classification Search
CPC ......... A61B 5/085; A61B 5/087; A61B 5/091; A61M 16/00; A61M 16/0003; (Continued)

(56) References Cited

U.S. PATENT DOCUMENTS 2,972,345 A 2/1961 Spigel
3,530,873 A 9/1970 Arp
(Continued)

FOREIGN PATENT DOCUMENTS

EP 0282675 A2 9/1988
EP 0283141 A2 9/1988
(Continued)

OTHER PUBLICATIONS

EP Appln. No. 08766977.6, Extended European Search Report, dated Aug. 7, 2014, pp. 1-13.
(Continued)

*Primary Examiner* — Annette Dixon
(74) *Attorney, Agent, or Firm* — Dann Dorfman Herrell and Skillman, P.C.

(57) ABSTRACT

A resuscitation device is disclosed that includes a pump having a cylinder with a gas inlet and a gas outlet, a piston to travel in the cylinder, and a valve. The valve is configured to allow gas to be displaced into the cylinder through the gas inlet during a first stroke direction and second stroke direction of the piston in the cylinder, and for allowing gas to be displaced through the gas outlet during an opposite of the first stroke direction and second stroke direction of the piston in the cylinder; a motor, selected from one of a stepper motor, a feedback motor, a stepper motor with feedback, and a linear motor, connected to the piston to move the piston in the cylinder; and a patient interface in fluid connection with the pump to receive gas via the gas outlet and to deliver the gas to a patient.

19 Claims, 11 Drawing Sheets

Related U.S. Application Data continuation of application No. 12/602,292, filed as application No. PCT/NZ2008/000128 on May 30, 2008, now abandoned.

(51) Int. Cl.
*A61M 16/04* (2006.01)
*A61M 16/20* (2006.01)
*A61M 16/08* (2006.01)
*A61M 16/12* (2006.01)

(52) U.S. Cl.
CPC ........ *A61M 16/04* (2013.01); *A61M 16/0666* (2013.01); *A61M 16/20* (2013.01); *A61M 16/201* (2014.02); *A61M 16/205* (2014.02); *A61M 16/209* (2014.02); *A61M 16/0048* (2013.01); *A61M 16/06* (2013.01); *A61M 16/0875* (2013.01); *A61M 16/12* (2013.01); *A61M 16/208* (2013.01); *A61M 2016/003* (2013.01); *A61M 2016/0015* (2013.01); *A61M 2016/0027* (2013.01); *A61M 2016/0036* (2013.01); *A61M 2202/0208* (2013.01); *A61M 2205/073* (2013.01); *A61M 2205/106* (2013.01); *A61M 2205/3334* (2013.01); *A61M 2205/3341* (2013.01); *A61M 2205/3368* (2013.01); *A61M 2205/502* (2013.01); *A61M 2230/06* (2013.01); *A61M 2230/42* (2013.01); *A61M 2230/432* (2013.01)

(58) Field of Classification Search
CPC .......... A61M 16/0009; A61M 16/0045; A61M 16/0048; A61M 16/0051; A61M 16/0069; A61M 16/0072; A61M 16/0075; A61M 16/0096; A61M 16/021; A61M 16/022; A61M 16/024; A61M 16/026; A61M 16/04; A61M 16/06; A61M 16/0666; A61M 16/085; A61M 16/0875; A61M 16/107; A61M 16/12; A61M 16/16; A61M 16/20; A61M 16/201; A61M 16/204; A61M 16/205; A61M 16/208; A61M 16/209; A61M 16/22; A61M 2016/0015; A61M 2016/0027; A61M 2016/003; A61M 2016/0036; A61M 2202/0208; A61M 2205/073; A61M 2205/106; A61M 2205/3334; A61M 2205/3341; A61M 2205/3368; A61M 2205/502; A61M 2230/06; A61M 2230/42; A61M 2230/432; A61M 2230/46; G05B 19/231; G05B 2219/33324; G05B 2219/34215; G05B 2219/37399; G05B 2219/41309; G05B 2219/42162; G05B 2219/42237; Y10T 137/7907; Y10T 403/7045; Y10T 74/16; Y10T 74/20828

See application file for complete search history.

(56) References Cited

U.S. PATENT DOCUMENTS

| | | | |
|---|---|---|---|
| 3,590,815 A * | 7/1971 | Schiff | A61M 60/43 |
| | | | 601/153 |
| 3,734,092 A | 5/1973 | Kipling | |
| 3,812,878 A | 5/1974 | Bird | |
| 3,905,362 A * | 9/1975 | Eyrick | A61M 16/024 |
| | | | 128/202.22 |
| 4,036,221 A * | 7/1977 | Hillsman | A61M 16/0009 |
| | | | 128/204.23 |
| 4,112,938 A * | 9/1978 | Jeretin | A61M 16/0045 |
| | | | 128/204.23 |
| 4,215,681 A | 8/1980 | Zalkin | |
| 4,297,999 A | 11/1981 | Kitrell | |
| 4,448,192 A * | 5/1984 | Stawitcke | A61M 16/0051 |
| | | | 128/204.23 |
| 4,527,557 A | 7/1985 | De Vries | |
| 4,719,910 A | 1/1988 | Jensen | |
| 4,773,305 A | 9/1988 | Nissels | |
| 4,844,085 A * | 7/1989 | Gattinoni | A61B 5/091 |
| | | | 600/533 |
| 5,092,326 A | 3/1992 | Winn et al. | |
| 5,107,830 A | 4/1992 | Younes | |
| 5,119,810 A * | 6/1992 | Kiske | A61M 16/022 |
| | | | 128/203.12 |
| 5,331,995 A | 7/1994 | Westfall | |
| 5,788,624 A | 8/1998 | Lu et al. | |
| 5,915,382 A | 6/1999 | Power | |
| 6,152,131 A | 11/2000 | Heinonen | |
| 6,182,658 B1 | 2/2001 | Hayek | |
| 6,264,432 B1 | 7/2001 | Kilayko et al. | |
| 8,230,857 B2 | 7/2012 | Cewers | |
| 2001/0037071 A1* | 11/2001 | Lingo, Jr. | A61B 5/091 |
| | | | 600/538 |
| 2002/0020414 A1 | 2/2002 | Fukunaga | |
| 2006/0021620 A1 | 2/2006 | Calluaud et al. | |
| 2006/0283450 A1 | 12/2006 | Shissler | |

FOREIGN PATENT DOCUMENTS

| | | |
|---|---|---|
| EP | 0700689 A2 | 3/1996 |
| JP | 3044396 | 10/1997 |
| JP | 2006006984 A | 1/2006 |
| RU | 2141855 C1 | 11/1999 |
| RU | 2219964 C2 | 12/2003 |
| SU | 314522 A | 3/1972 |
| WO | 1995032753 A1 | 12/1995 |
| WO | 2007055829 A2 | 5/2007 |

OTHER PUBLICATIONS

International Search Report dated Sep. 18, 2008 of International Application No. PCT/NZ2008/000128.

International Preliminary Report on Patentability dated Sep. 8, 2009 of International Application No. PCT/NZ2008/000128.

* cited by examiner

ELECTRICALLY OPERABLE RESUSCITATORS

CROSS REFERENCE TO RELATED APPLICATIONS

This application is a continuation of U.S. application Ser. No. 14/741,848, filed on Jun. 17, 2015, which was a continuation of U.S. application Ser. No. 12/602,292, filed on Feb. 26, 2010, which was the National Stage of International Application No. PCT/NZ2008/000128, filed on May 30, 2008, the entireties of which are incorporated herein by reference.

FIELD OF THE INVENTION

The present invention relates to improvements to resuscitators.

BACKGROUND TO THE INVENTION

Resuscitators that can supply pressurised air or oxygen to a patient are well-known. Examples include bag or bellows type resuscitators and pump-like resuscitators and pressure-limited resuscitators. However, there are limitations in certain resuscitators. For example, there is a risk of overinflating a patient's lungs by delivering a volume of air that is greater than desirable. There is also a risk the pressure of the air or oxygen delivered may be at undesirably high levels. Such undesirable characteristics of the air being delivered to the patient can have adverse affects on the patient. If a patient's airway passage is or becomes blocked and air is delivered by the known devices then undesirable pressures may be reached. Further such increased pressure may cause sudden dislodgement of the blockage and may lead to serious consequences for the patient. Known devices do not readily lend themselves to predetermination of airway pressures and volumes to which the lungs of the patient are being subjected by the operator of the device. The operator may feel a resistance when they are applying a force to the device to deliver air or oxygen. The operator may increase the force to overcome the blockage. However, when the blockage clears there is a risk of over-pressurising or overfilling the lungs, thereby causing barotrauma or volutrauma or both.

Eliminating human operation of a resuscitator for delivering air to a patient is advantageous. By eliminating the operator the risk of delivering too great a volume of air into the patient and overinflating the patient's lungs, causing volutrauma, is reduced. By eliminating the operator the risk of delivering too great a pressure of air into the patient and therefore over pressurising the patient's lungs, causing barotrauma, is reduced. In resuscitation it is desirable to start at the lowest risk procedure to the patient. The lowest risk procedure is volume resuscitation rather than pressure-limited resuscitation or manual-controlled resuscitation.

In known devices there is the risk that an operator may displace too great a volume of air into the patient and therefore overinflate the patient's lungs. There is also the risk of applying a pressure that is too great for the patient's lungs. For example, when the airway passage is blocked, prior art systems do not signal that the operator should stop and remove the blockage.

It would therefore be an advantage to provide improvements to resuscitators that addresses or goes at least someway towards addressing at least some of the abovementioned disadvantages and/or addresses at least some of the abovementioned advantages or that will at least provide the public or industry or both with a useful choice.

SUMMARY OF THE INVENTION

Accordingly in a first aspect the present invention consists in an electrically operable resuscitation device comprising:
(a) a pump including
a rigid cylinder including at least one gas inlet and at least one gas outlet,
a piston to travel in said cylinder, and
at least one valve, the or each valve configured for allowing gas to be drawn into said cylinder through said at least one gas inlet during at least one of a first stroke direction and/or a second stroke direction of said piston in said cylinder, and for allowing gas to be displaced through said at least one gas outlet during an opposite of at least one of the first stroke direction and/or second stroke direction of said piston in said cylinder,
(b) accurate positional control motor preferably selected from a stepper motor and feedback motor or a stepper motor with feedback and linear motor, operatively connected to said piston to move said piston in said cylinder with accurate velocity control,
(c) a patient interface in ducted fluid connection with said pump to receive gas via said at least one gas outlet and to deliver said gas to said patient.

Preferably said patient interface is a face mask or endotracheal tube or naso-tube.

Preferably said motor is a linear stepper motor that may also have feedback.

Preferably said motor is a servo motor that may also have feedback.

Preferably said motor is a linear stepper motor and is directly connected to said piston.

Preferably the motor is indirectly connected with said piston, via a linkage.

Preferably said piston includes a connection rod with which said motor is in operative connection.

Preferably said piston is or includes one part (eg an iron bar and rare earth magnet assembly) of the two moving part linear motor.

Preferably the motor and cylinder are connected together (and are preferably engaged to each other).

Preferably wherein intermediate of the patient interface and the at least one outlet of the cylinder and in said ducted fluid connection therewith is a gas flow controller.

Preferably the gas flow controller includes a one way valve that allows gas to be displaced from the outlet of the cylinder towards the patient interface and prevents gas from flowing through the one way valve in the opposite direction.

Preferably the gas flow controller includes a valved exhaust port via which gas can exhaust to relieve pressure at the patient interface.

Preferably said valved exhaust port assumes a closed condition when the piston is moving in a direction to displace gas towards the patient interface and assumes an open condition when the piston is moving in the opposite direction to allow gas due to exhalation of or by the patient to pass through the exhaust port.

Preferably said valved exhaust port includes at least one opening closable by a valve, said valve mounted on or to or in operative association with an actuator to actively control the movement of the valve relative the opening.

Preferably said valved exhaust port includes at least one opening closable by a valve, said valve mounted for movement relative the opening in a passive manner under the influence of pressure differential in the gas from controller and/or between the gas flow controller and ambient gas pressure.

Preferably said valved exhaust port is moved to a closed condition when gas is to be displaced into said patient and to an open condition to allow gas due to exhalation of or by the patient to pass through the exhaust port.

Preferably said valved exhaust port includes at least one opening closable by a valve, said valve mounted on or to or in operative association with an actuator to actively control the movement of the valve relative to the opening.

Preferably said valved exhaust port includes at least one opening closable by a valve, said valve mounted for movement relative the opening in a passive manner under the influence of pressure differential in the gas from controller and/or between the gas flow controller and ambient gas pressure.

Preferably when the valved exhaust port is in the open condition, said motor stops or reduces the velocity of the piston.

Preferably a controller is coupled to said motor to control at least the velocity and position of the motor.

Preferably said controller is coupled to said actuator to move said actuator preferably in a manner in synchronicity with control of said motor.

Preferably a source of electricity is connected to said motor.

Preferably said source of electricity is connected to said motor via said controller.

Preferably via an interface, the controller can be instructed to operate the device in a suitable manner.

Preferably the interface allows for patient-related information to be entered into the controller, the information including at least one selected from a patient's age and weight.

Preferably the controller receives data from other parts of the device, including at least one of gas pressure at the patient interface and tidal volume flow rate at the patient interface.

Preferably a display is provided to display operating conditions of said device.

Preferably the operating conditions displayed may include inlet gas pressure, patient interface gas pressure, tidal volume at the patient interface, piston oscillation rate, piston stroke length, battery power, duration operation.

Preferably the operating conditions may also be recorded for subsequent reference.

Preferably fluid connection between said outlet of said cylinder and the patient interface is defined in part by a flexible conduit.

Preferably fluid connection between said outlet of said cylinder and the patient interface is defined in part by a flexible conduit and said flow controller is located more proximate said patient interface than said cylinder.

Preferably the ducted fluid connection and/or the patient interface includes a pressure relief valve to allow pressure reduction of gas in said patient interface.

Preferably the pressure relief valve becomes operative to relieve pressure when the pressure in said patient interface reaches a certain threshold.

Preferably said pump includes an inlet volute.

Preferably the inlet volute includes an opening to allow pressure relief of said inlet volute to occur.

Preferably said inlet volute includes a one way valve to allow pressure relief to occur into the inlet volute.

Preferably the said inlet volute includes a pressure relief valve to allow pressure relief to occur out of said inlet volute.

Preferably said inlet of said cylinder is in fluid connection with a supplementary gas supply to allow gas from said supplementary gas supply to pass into said cylinder for subsequent delivery to the patient. More preferably, the gas is oxygen.

Preferably said cylinder is split into two zones by said piston, a first zone being on one side of said piston and a second zone being on the other side of said piston and wherein said gas inlet(s) are provided to allow gas into the first zone and said gas outlet(s) are provided to allow gas out of said second zone, wherein a one way pump valve is provided to allow gas to transfer from said first zone to said second zone and that restricts flow in the opposite direction.

Preferably the one way pump valve is carried by the piston to operate on a passage through the piston.

Preferably gas in said first zone, is or becomes pressurised sufficiently to, upon the movement of the piston in its first stroke direction, allow some of the gas to displace through the one way pump valve into the second zone.

Preferably the one way pump valve is a passive one way valve that moves between an open and closed condition dependent on pressure differential across the one way pump valve.

Preferably a one way valve (inlet one way valve) may be provided to allow gas to be drawn into the first zone upon the movement of the piston in its second stroke direction and that restricts flow of gas in the opposite direction through said inlet one way valve upon the movement of the piston in the first stroke direction.

Preferably the inlet one way valve is a passive one way valve that moves between an open and closed condition dependent on pressure differential across the inlet one way valve.

Preferably one or each of the one way valves mentioned are valves under active control to be in the open and closed conditions in correspondence with the direction of movement of the piston.

Preferably the cylinder and piston stroke length are of a size to allow a sufficient volume of gas to be displaced from said cylinder through said gas outlet(s) during said second direction of movement of the piston to deliver a desired volume and flow rate of gas for a single inhalation to a neonatal patient for resuscitation purposes.

Preferably said cylinder is split into two zones by said piston, a first zone being on one side of said piston and a second zone being on the other side of said piston, and wherein the pump is a double acting pump that includes:
  (a) a first one way valve to
    i) allow gas to enter into the first zone via a said gas inlet (herein after "first gas inlet") of said cylinder during movement of the piston in its second direction of movement, and
    ii) restrict gas flow in the opposite direction through said first gas inlet during movement of the piston in the first direction of movement
  (b) a second one way valve to
    i) allow gas to exit the first zone via a said gas outlet (herein after "first gas outlet") of said cylinder during movement of the piston in its first direction of movement, and
    ii) restrict gas flow in the opposite direction through said first gas outlet during movement of the piston in the second direction of movement
  (c) a third one way valve to i) allow gas to enter into the second zone via a said gas inlet (herein after "second gas inlet") of said cylinder during movement of the piston in its first direction of movement, and ii) restrict gas flow in the opposite direction through said second gas inlet during movement of the piston in the second direction of movement (d) a fourth one way valve to i) allow gas to exit the second zone via a said gas outlet (herein after "second gas outlet") of said cylinder during movement of the piston in its second direction of movement, and ii) restrict gas flow in the opposite direction through said second gas outlet during movement of the piston in the first direction of movement (e) a manifold or ducting to duct gas from said first and second outlets to said patient interface.

Preferably each of at least one of the first to fourth one way valves are either actively controlling or passive in moving between their open and closed conditions.

Preferably the cylinder and piston stroke length are of a size, and the motor is able to move and be controlled, to allow a sufficient volume of gas to be displaced from said cylinder through said gas outlet(s) during multiple oscillations of the piston to deliver a desired volume and flow rate of gas for a single inhalation to a patient for resuscitation purposes or ventilation purposes or both.

Preferably the pump is a double acting pump and the motor is of a sufficient speed to, in multiple stokes of the piston, deliver a single tidal volume of gas for a single inhalation to a patient for ventilation and/or resuscitation purposes.

Preferably the device is portable.

Preferably at least one of the pump and patient interface and motor are portable and preferably unitary and preferably able to be held in one hand by a user.

Preferably at least one of the controller and power supply and display are also portable and preferably unitary and preferably able to be held in one hand by a user.

Preferably communication to and from the controller may be wireless.

In a second aspect the present invention consists in a resuscitator to deliver gas to a patient to be resuscitated that includes a positive displacement pump that is operated by a linear motor.

Preferably the pump is of a kind to allow continuous displacement gas to a patient to occur during operation of the pump and the velocity of linear motor is controlled to displace gas to the patient in a manner to facilitate resuscitation.

Preferably the control of the linear motor is such as to change its velocity to provide a variation in the volume of gas delivered.

Preferably the pump is a positive displacement pump (preferably a piston and cylinder pump).

Preferably the linear motor actuates the piston for multiple oscillations to deliver a single tidal volume of gas to the patient.

In a further aspect the present invention consists in a gas flow controller for a resuscitator that includes a pump to pressurise a gas for delivery to a patient and a patient interface, the controller interposed between said pump and interface and including a one way valve that allows gas to be displaced from the pump towards the patient interface and prevents gas from flowing through the one way valve in the opposite direction.

Preferably the gas flow controller includes a valved exhaust port via which gas can exhaust to relieve pressure at the patient interface.

Preferably said valved exhaust port assumes a closed condition when the pump is operating in a mode to displace gas towards the patient interface and assumes an open condition during exhalation of or by the patient to pass allow exhaled gas to pass through the exhaust port.

Preferably, said valved exhaust port assumes an open condition when the device is in a non-operative or non-operational mode. More preferably, the valved exhaust port assumes an open condition when the pump is in a non-operative or non-operational mode.

Preferably said valved exhaust port includes at least one opening closable by a valve, said valve mounted on or to or in operative association with an actuator to actively control the movement of the valve relative the opening.

Preferably said valved exhaust port includes at least one opening closable by a valve, said valve is mounted for movement relative the opening in a passive manner under the influence of pressure differential in the gas from controller and/or between the gas flow controller and ambient gas pressure.

Preferably said valved exhaust port is moved to a closed condition when gas is to be displaced into said patient and to an open condition to allow gas due to exhalation of or by the patient to pass through the exhaust port.

Preferably said valved exhaust port includes at least one opening closable by a valve, said valve mounted on or to or in operative association with an actuator to actively control the movement of the valve relative the opening.

Preferably said valved exhaust port includes at least one opening closable by a valve, said valve mounted for movement relative the opening in a passive manner under the influence of pressure differential in the gas from controller and/or between the gas flow controller and ambient gas pressure.

In a further aspect the present invention consists in a resuscitator device that operates to define an inhalation period during which a gas is displaced from the device to the patient and an exhalation period where no gas is displaced from the device to the patient and any gas received from the patient is exhausted from the device, wherein the device utilises an accurate positional control motor (eg a linear motor or rotary stepper motor) that controls a pump, the motor being controlled to operate the pump during the inhalation period and the motor being controlled to stop the pump during the exhalation period.

Preferably the pump undertakes a plurality of oscillations during any one inhalation period.

Preferably the pump undertakes no more than one oscillation during any one inhalation period.

In a further aspect the present invention consists in a resuscitator as herein before described and as herein described with reference to the accompanying drawings.

In a further aspect the present invention consists in a resuscitator as herein described with reference to the accompanying drawings.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

As used herein the term "and/or" means "and" or "or", or both. As used herein "(s)" following a noun means the plural and/or singular forms of the noun.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

BRIEF DESCRIPTION OF THE DRAWINGS

A preferred form of the present invention will now be described with reference to the accompanying drawings in which.

DETAILED DESCRIPTION OF PREFERRED EMBODIMENTS

Figure 1:
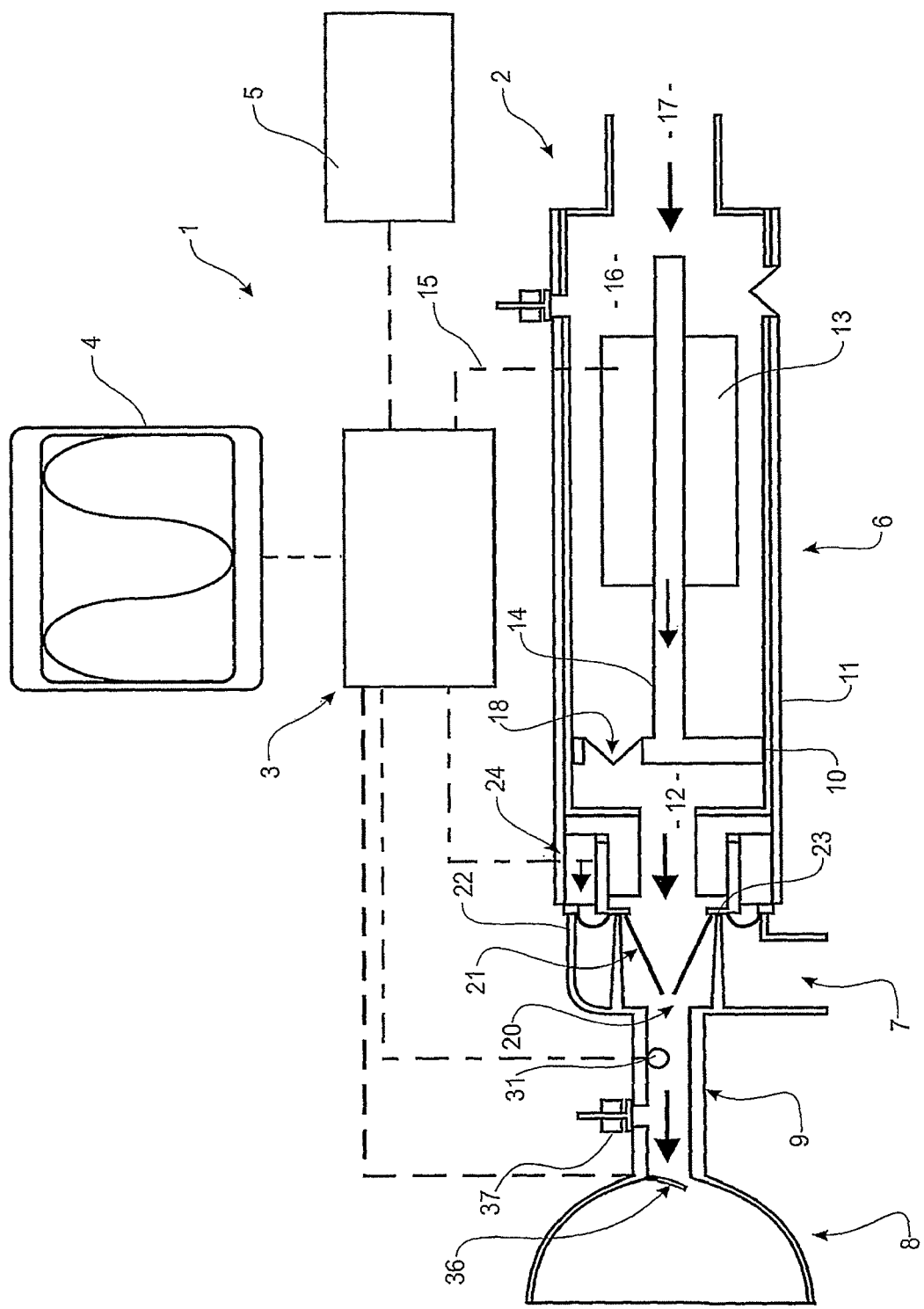
FIG. 1 is a schematic view of a resuscitator and is shown to describe it being in the inhalation phase.

With reference to FIG. 1, there is shown a resuscitator 1. The resuscitator 1 consists of a resuscitator body 2. It may also include associated hardware such as a controller 3, a display panel 4 and power supply 5 connected to each other and/or the resuscitator body 2.

The resuscitator body 2 consists of a pump unit 6, a flow control unit 7 and a patient interface 8.

Broadly speaking the pump unit 6 includes a pump that will deliver air to the flow control unit 7. The flow control unit 7 will control the flow of gas between the patient interface and the flow control unit 7 in conjunction with or without the pump unit 6 depending on the status of operation of the resuscitator 1.

In the most preferred form the pump unit 6 and flow control unit 7 are part of the same body as for example shown in FIG. 1. A conduit 9 extending between the flow control unit 7 and the patient interface 8 facilitates the flow of gas between the interface and the flow control unit 7.

In the examples shown in the accompanying drawings, the interface is preferably a face mask. However, alternatively, the interface may be an endotracheal tube or nasotube that extends partly into the patient's airway.

The pump unit 6 consists of a piston 10 that locates in a cylinder 11 to displace gas through an outlet opening 12 of the cylinder and to the flow control unit 7. The piston and cylinder are a complementary shape and make sure that a sufficiently tight seal exists between the piston and cylinder for the purposes of positively displacing gas through the outlet opening 12.

The cylinder 11 may be cylindrical in cross-section or may be any other shape in cross-section.

The piston is actuated via its connection rod 14, by a motor 13. In the most preferred form the motor is an actuator preferably a linear motor. In an alternative form the actuator may be a servomotor, stepper motor or similar device. The connection rod 14 may be the reactor to operate in conjunction with the motor 13 for the purposes of displacing the piston 10 in the cylinder 11 in an oscillating manner. Alternatively the connection rod 14 may carry a reactor plate or surface in conjunction with the motor 13. In the figures, the connection rod 14 is acted upon directly by the motor 13. The reactor plate may also be incorporated as part of the piston to be integral therewith. No connection rod may then be provided. Alternative mechanisms may be employed where such action is indirect via a linkage mechanism. Such linkage may include a rotor and crank and connection rod.

In the most preferred form the motor 13 is a linear motor or any other motor that has accurate and rapid positional control capabilities. The controller 3 via a connection 15 with the motor 13 will operate the motor in a manner so that the desired flow rate, volume and pressures are being delivered through the outlet opening 12.

The flow control unit 7 consists of an inlet that may coincide with or define the outlet opening 12 of the pump unit. The flow control unit includes an outlet 20 and a passage extending between the inlet and outlet. The passage allows the transmission of gas being displaced from the pump unit 6 to the outlet 20. The outlet 20, preferably via a conduit 9, allows the delivery of this gas to the patient interface 8.

Intermediate of the inlet and outlet of the flow control unit is a one-way valve 21. The one-way valve allows for gas to travel from the inlet towards the outlet via the passage but prevents flow of gas from the outlet to the inlet.

The valve 21 may be mounted in a fixed manner to the housing 22 of the flow control unit 7 or alternatively and as shown in FIG. 1, may be mounted to a movable mount 23 to move the valve mount.

Figure 2:
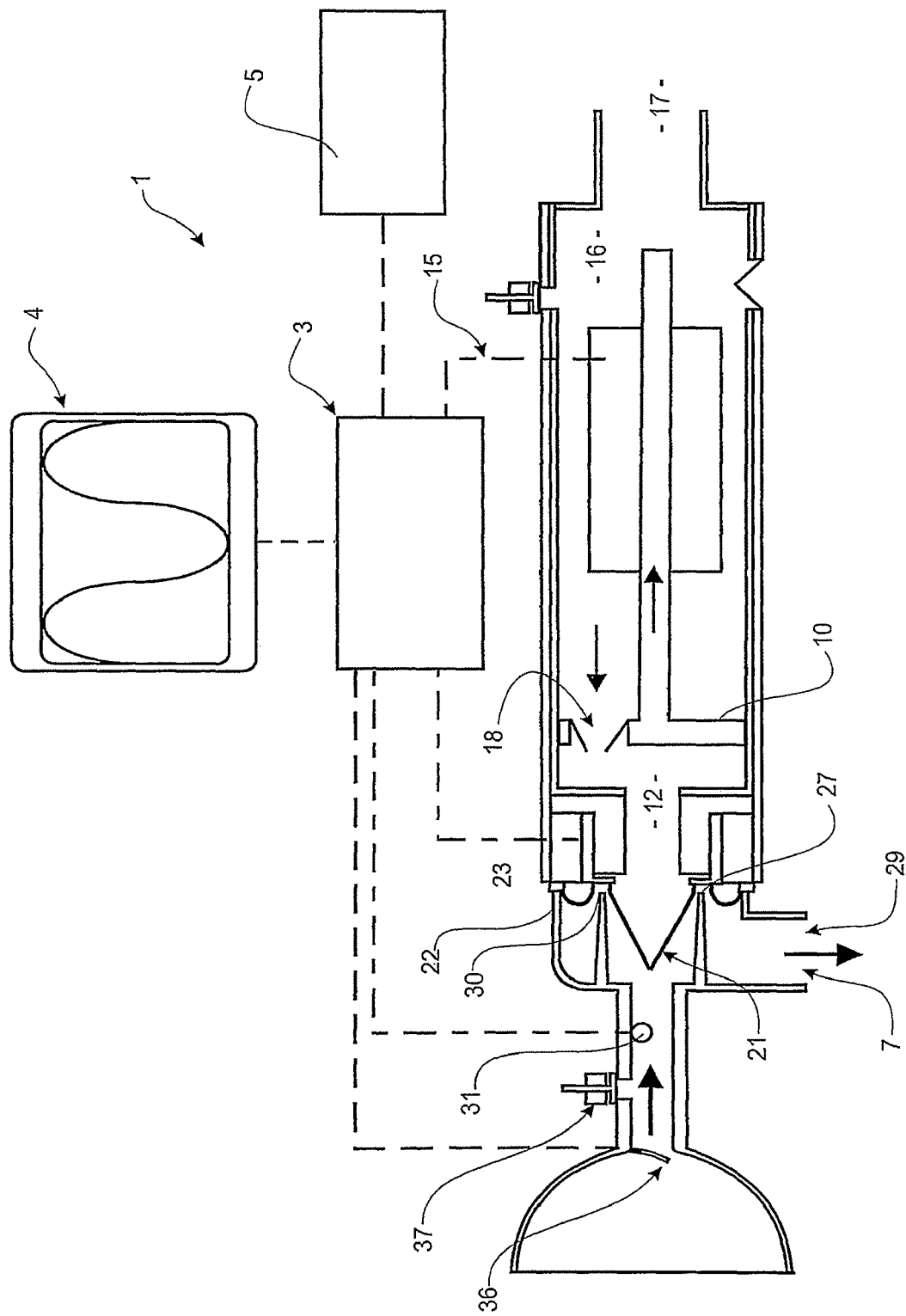
FIG. 2 is a schematic view of a resuscitator and is shown to describe it in the exhalation phase.

In the preferred form the movable mount 23 forms part of a voice coil actuator 24 that can displace the movable mount 23 between two positions. The first position is as shown in FIG. 1 and the second position is as shown in FIG. 2. This creates a valve referred to herein as the exhalation or exhaust valve. In FIG. 1 the moveable mount 23 is located in a position so that at least on the outlet 20 side of the valve 21, no other opening to the passage of the flow control unit 7 is created. All gas that is displaced by the pump unit 6 is captured for flow towards the patient interface 8.

In the second position of the mount as shown in FIG. 2, an opening 27 is created between part of the housing 22 of the flow control unit 7 and the moveable mount 23. In this position gas can escape from that part of the passage of the flow control unit 7 intermediate of the valve 21 and the flow control unit outlet 20. In this position of the moveable mount 23, gas that may be exhaled from the patient can travel through the opening 27 for example towards the surrounding atmosphere through opening 29. The opening 27 may be an annular opening that is created between a substantially disk shaped mount portion and a circular shaped seat 30 of the housing 22 of the flow control unit 7.

As a consequence of a pressure differential between the patient side and pump side of the one-way valve 21, the one-way valve 21 will assume a closed position as shown in FIG. 2 during the exhalation operating phase of the resuscitator. This negative pressure differential may be established by one or more of a combination of the patient breathing out, the retraction of the piston in its cylinder away from the outlet opening 12 and the movement of the voice coil actuator 24 in a direction establishing the opening 27. In the most preferred form it is the voice coil actuator 24 that primarily establishes the open and closed condition between the opening 27 and that part of the passage of the flow control unit 7 between the flow control unit outlet 20 and the one-way valve 21. However where a patient is breathing on their own and is able to create sufficient pressure, movement of the moveable mount 23 of the valve 21 to create the opening 27 may occur without assistance of the voice coil actuator. It will be appreciated that other actuators may be used. Actuators that move other components other than the valve 21 to create such an opening for exhaled gases to be discharged may be used.

In the exhalation operating phase of the resuscitator, the piston is withdrawn by the motor 13 preferably back to a predetermined start position. The piston retracts once it has travelled its full desired stroke during the inhalation operating phase and has delivered the required tidal volume or has timed out while holding the maximum airway pressure during the inhalation period. Control of the position or movement of the voice coil actuator 24 can occur by the controller 3 and is preferably synchronised with movement of the piston.

In a "PEEP" mode (positive end expiratory pressure) parameters can be preset by using the controller or the display panel PEEP so that pressure is controlled by the voice coil actuator. The voice coil actuator 24 will exert a closing force to the exhalation valve equal to the predetermined PEEP pressure. The PEEP pressure is measured by the airway pressure sensor 31. The controller 3 will activate the voice coil actuator 24 when the expiratory airway pressure has reached the predetermined level.

In operation of the resuscitator shown in FIGS. 1 and 2, the tidal volume delivered to the patient can be preset by the controller 3 or the display panel 4. The tidal volume is controlled by the stroke length of the piston 10. Tidal volume is delivered to the patient on the compression stroke of the piston 10 and exhalation for the patient is facilitated during the retraction stroke of the piston 10. Accordingly one inhale and exhale of the patient occurs during a movement of the piston 10 from one starting point to its opposite end travel and back to the starting point. For a given cylinder size, the longer the stroke of the piston, the greater the tidal volume.

The controller 3 instructs the motor 13 to move the piston 10 a predetermined distance at a predetermined velocity.

Feedback from the airway pressure sensor 31 and a flow and tidal volume sensor 36 can provide further control. These sensors may vary normal operation of the piston 10 and/or voice coil actuator 24 from conditions of operation predetermined by an operator and instructed to the device via the display panel 4 and/or controller 3. The stroke length and position of the piston 10 may in addition be monitored by a sensor (a piston position sensor) of or associated with the motor 13 and/or piston 10. The operation of the resuscitator will control the breath rate and inhalation/exhalation ratio. This can be preset by using the controller and/or display panel and may be controlled at least in part by a timer of the controller. Patient dependent parameters may also control operation. For example, input information into the controller 3 may include a patient's weight and age.

In a situation where the airway pressure sensor 31 senses that the maximum predetermined airway pressure has been reached, the controller 3 can instruct the motor 13 to slow or stop. This can result in a maintaining of the maximum predetermined airway pressure for the duration of the inhalation time period. In the event of an overpressure or system failure, a safety valve 37 may be actuated to open and relieve pressure on the patient airway. The safety valve 37 may be a passive valve that has predetermined operating conditions. Alternatively it may be a safety valve connected with the controller 3 and controlled by the controller for operation. Alternative to the safety valve 37, the airway pressure sensor 31 and/or flow and tidal volume sensor 36 may communicate with the controller 3 to direct movement of the voice coil actuator in instances where undesirable conditions are being sensed to thereby relieve pressure and/or flow by exhausting gas through the opening 29.

This first form of resuscitator described as well as the form yet to be described allows for data from the airway pressure sensor 31, the piston position sensor, the flow and tidal volume sensor 36 and from a timer to be used to record operating data and performance. A graphical display on the display panel 4 can also be generated. The graphical display can be used by the operator to monitor performance and determine if leakage, blockage or further adjustments are required to the resuscitator. The graph and/or related data can be stored to assist in the setup of other life support systems and for clinical analysis. Such statistical information may offer significant benefits to future situations.

The electrical connection 15 will ensure that the controller 3 can appropriately control the linear motor to thereby control the position and movement of the piston. The cylinder 11 has an inlet volute 16 that includes a primary inlet 17. It is through the primary inlet that ambient air may be drawing into the inlet volute as the piston displaces inside the cylinder towards the outlet opening 12. This direction of travel is shown in FIG. 1. The piston 10 carries a one-way valve 18 that operates to be in a closed condition when the piston is travelling towards the outlet opening 12. This will result in a drawing of ambient air into the inlet volute 16. When the piston 10 travels in the opposite direction being an exhalation direction of the resuscitator, the one-way valve 18 can open to allow for air in the inlet volute 16 to displace into the region between the piston 10 and the outlet opening 12 as for example shown in FIG. 2. The primary inlet 17 may include a one-way valve to assist such displacement through the opening created by the one-way valve through the piston by preventing air in the inlet volute 16 from displacing back out through the primary inlet 17. The gas that has displaced into the space between the piston 10 and the outlet opening 12 can then on the return stroke during the inhalation phase of operation be displaced at least in part through the outlet opening 12 and to the flow control unit 7.

The resuscitator may (for example shown in FIG. 3) operate in a supplementary oxygen and C-pap mode. A supplementary gas reservoir 40 (that may or may not be connected to supplementary supply via the inlet 41) can be engaged to the primary inlet 17 of the pump unit 6. Rather than drawing ambient air into the pump unit, the oxygen or other gas or gas mixture can be supplied to a patient via the resuscitator. This will allow the operator to control the delivery of an air/oxygen mixture by the use of for example an external blender. Supplementary gas such as oxygen may be delivered via the primary inlet 17 to the pump unit, under pressure. In the event of a failure or the gas supply exceeding the capabilities of the resuscitator, then a safety valve 42 may open to exhaust gas from at least part of the pump unit 6. A pressure sensor may be located in an appropriate location for these purposes. If a failure occurs with the supplementary gas supply or the primary inlet 17 becomes blocked then a safety valve 43 may open to allow for ambient air to be drawn into the pump unit 6 allowing ongoing operation of the resuscitator despite issues with the supply of supplementary gas.

In a C-pap mode operational conditions can be specified and preset by using the controller and/or display panel. Where the delivery rate and pressure to the supplementary gas reservoir 40 is set at an appropriate flow level, the ventilator can operate in the C-pap mode. The motor 13 will stop operation and the flow from the supplementary gas reservoir 40 will pass through the one-way valve 18 through the one-way valve 21 to the patient interface 8. The airway pressure sensor 31 will determine the patient's airway pressure. When the predetermined C-pap pressure has been reached the voice coil actuator 24 will exert a closing force to the exhalation valve to the predetermined C-pap pressure.

Figure 3:
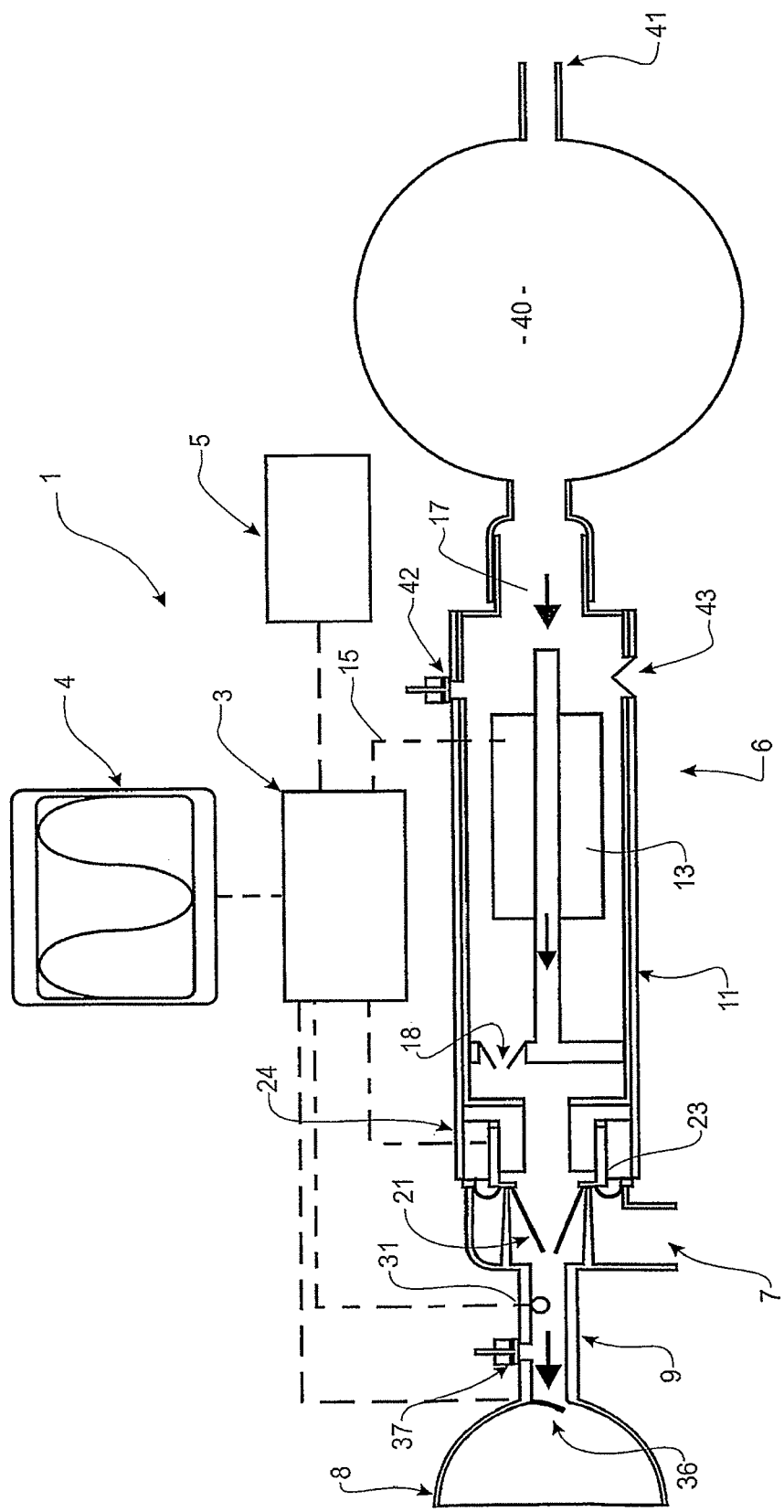
FIG. 3 shows the resuscitator in a C-pap mode wherein a supplementary gas is supplied to the resuscitator.
Figure 4:
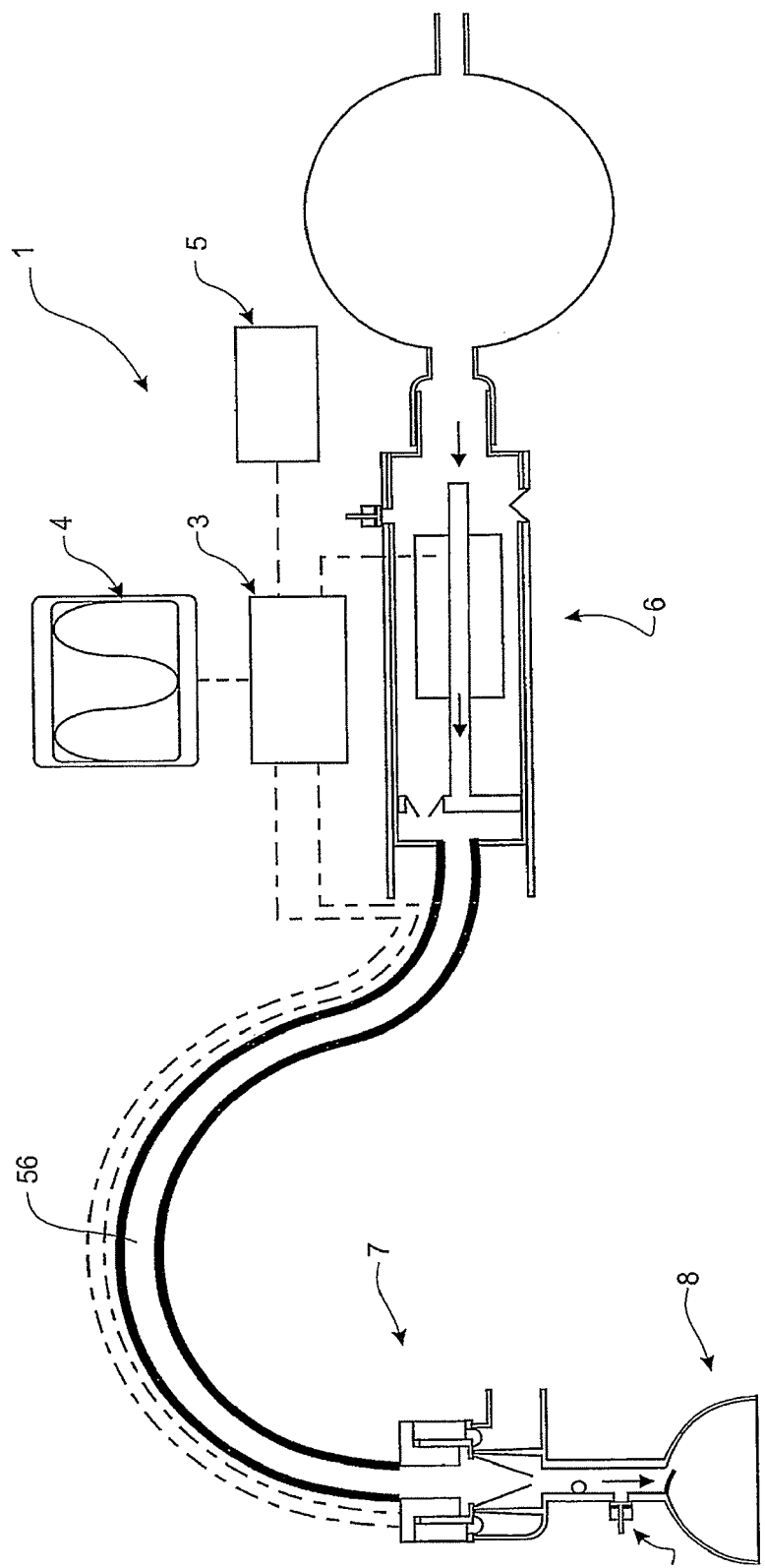
FIG. 4 is a schematic view of a variation of the resuscitator shown in FIGS. 1-3, also in a C-pap mode and wherein a flexible conduit extends between parts of the resuscitator to provide to some extent, independence of movement of the face mask relative some of the other components of the resuscitator.

With reference to FIG. 4 there is shown a variation to the resuscitator described with reference to FIGS. 1-3 wherein a flexible conduit 56 is provided to extend between the pump unit 6 and the flow control unit 7. The flexible conduit 56 may be fitted between the pump unit and the flow control unit to allow for delivery for gas displaced by the piston 10 towards the patient interface 8. Having the flow control unit 7 and airway pressure sensors and tidal volume sensors as well as the safety valve 37 close to the patient's airway, ensures a more accurate tidal volume and pressure delivery. Also the controller can make adjustments for the compliance in the patient mask. Also possible but less advantageous is to provide a conduit 9 that is of a desired length to allow for more distal location between the patient interface 8 and the pump unit 6. However this has the disadvantage of dead space between the features of the flow control unit 7 and the patient interface 8. The resuscitator of FIGS. 1-4, wherein the piston is single acting, lends itself particularly to resuscitation and ventilation of neonatal patients. A manageable sized pump unit can be provided wherein in one stroke of the piston a sufficient tidal volume of air can be delivered to a neonatal patient for inhalation. It is desirable for the unit to be relatively portable and therefore size can be a design constraint. However where size is not an issue, the pump unit 6 can be scaled up so that single compression stroke of the piston can deliver a sufficient tidal volume of gas to larger patients. However this will increase at least the size of the pump unit 6 making it less convenient for portability purposes.

An alternative configuration of resuscitator may be utilised where size can be smaller. This resuscitator is shown for example in FIG. 5. The resuscitator 101 includes a patient interface 108, flow control unit 107 and related components that are preferably the same as those described with reference to the resuscitator of FIGS. 1-4.

This alternative form of resuscitator also includes a pump unit 106. The pump unit 106 varies to the pump unit 6 described with reference to FIGS. 1-4. There is provided a motor 113 such as a linear motor or servo motor controlled by a controller 103 that may be engaged with a display panel 104. The linear motor operates a piston 110 via a connection such as a connection rod 114 that operates in a cylinder 111. The pump unit 106 includes an inlet volute 116. The inlet volute via a primary inlet 117 can draw air or supplementary gas supply therethrough as a result of the action of the piston and into the inlet volute 116.

The cylinder includes two openings capable of being in communication with the inlet volute 116. A first opening 160 is provided on the extension side of the piston 110. A second opening 161 is provided on the retraction side of the piston 110. The opening 160 is closable by a one-way valve 162. The opening 161 is closable by a one-way valve 163. The one-way valve 162 is able to assume an opening condition during the retraction stroke of the piston and is in a closed condition during the extension stroke of the piston. The one-way valve 163 is able to assume an open position during the extension stroke of the piston and is in a closed condition when the piston is retracting. On the extension side of the piston 110 is an outlet opening 164 of the cylinder 111. The outlet opening is closable by a one-way valve 165. The one-way valve 165 is in a closed condition during the retraction stroke of the piston and is able to assume an open condition during the extension stroke of the piston. The one-way valve 165 hence essentially works in an opposite mode to the one-way valve 162 to the cylinder. The outlet opening 164 is able to create a fluid connection of that part of the cylinder on the compression side of the piston with an outlet volute 166. The outlet volute 166 includes an outlet opening 112 through which gas displaced by the piston can pass to the flow control unit 7. The outlet volute 166 is separated from the inlet volute 116. The housing of the pump unit 106 may include both the inlet volute 116 and outlet volute 166 and partitions 167 and the cylinder 111 may separate the volutes. On the retraction side of the piston 110 the cylinder includes an opening 168 to the outlet volute 166. The opening 168 includes a one-way valve 169. The one-way valve is positioned so that during the retraction stroke of the piston, gas can displace on the retraction side of the cylinder through the one-way valve 169 into the outlet volute 166. The one-way valve 169 will assume a closed condition during the extension stroke of the piston 110.

Figure 6:
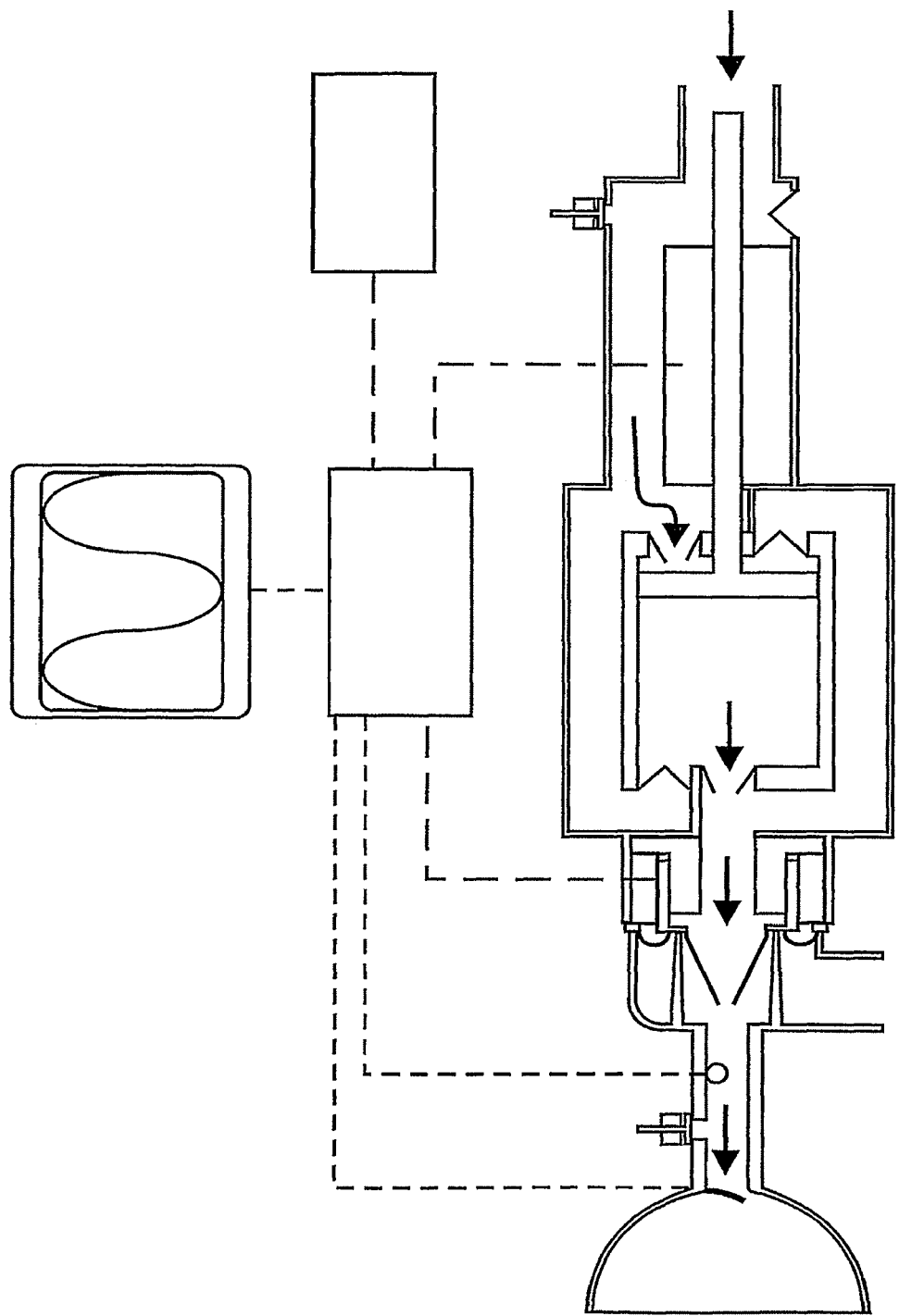
FIG. 6 is a schematic view of the resuscitator of FIG. 5 shown in operation, moving in an inhalation phase.
Figure 7:
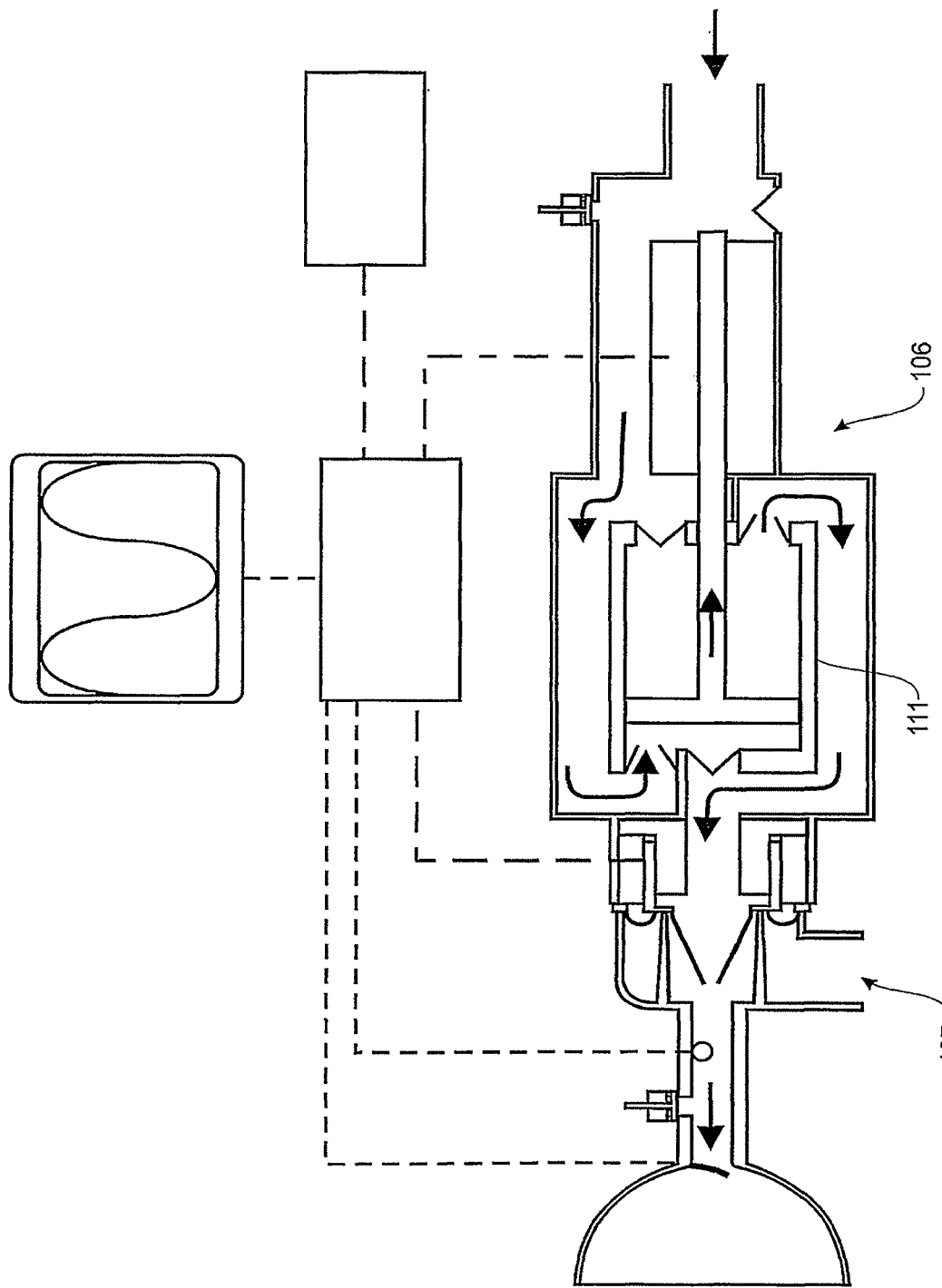
FIG. 7 is a schematic view of the resuscitator of FIG. 5 shown in an inhalation phase.

In operation during the extension stroke of the piston as shown in FIG. 6, the one way valve 163 opens allowing for air to be drawn into the retraction side of the cylinder. Air on the extension side of the piston during the extension stroke can be displaced through the one-way valve 165 to be delivered into the outlet volute. One-way valve 169 will be closed thereby only offering one outlet to the outlet volute 166 being the outlet opening 112. During the extension stroke of the piston the retraction side of the cylinder is charged with gas being drawn through the one-way valve 163. When the piston travels in its retraction stroke as shown in FIG. 7, gas that has been drawn into the retraction side of the cylinder may then be displaced through the one-way valve 169 into the outlet volute 166. The one-way valve 163 will close during the retraction stroke thereby creating only one outlet from the cylinder on its retraction side, namely the opening to discharge the gas into the outlet volute 166.

During the retraction stroke the one-way valve 165 is closed thereby offering only one outlet for gas being delivered into the outlet volute, namely being the outlet opening 112. During the retraction stroke the extension side of the cylinder is charged with gas from the inlet volute 116 via the one-way valve 162 that is in that condition opened. As can be seen the pump unit 106 hence operates in a double acting manner. Both during the extension and retraction stroke of the piston gas is displaced towards the outlet opening 112 for delivery towards the patient. With the use of a linear motor or servo motor having high frequency capabilities and accurate and immediate start and stop timing, a high frequency operating piston can deliver gas to the patient in effectively a continuous manner during both the retraction and extension strokes. Each tidal volume delivered to the patient may involve a high number of strokes of the piston. This allows for a compact and preferably portable unit to be provided. Upon exhalation of the patient the flow control unit 107 may be operated to open the exhaust valve to allow for exhalation to occur may coincide with the linear motor stopping operation. Alternatively the linear motor may continue oscillating the piston but where a waste valve may be opened to discharge displaced air from the piston from reaching the flow control valve. Alternatively such wasting may occur via the exhaust valve of the flow control.

Figure 5:
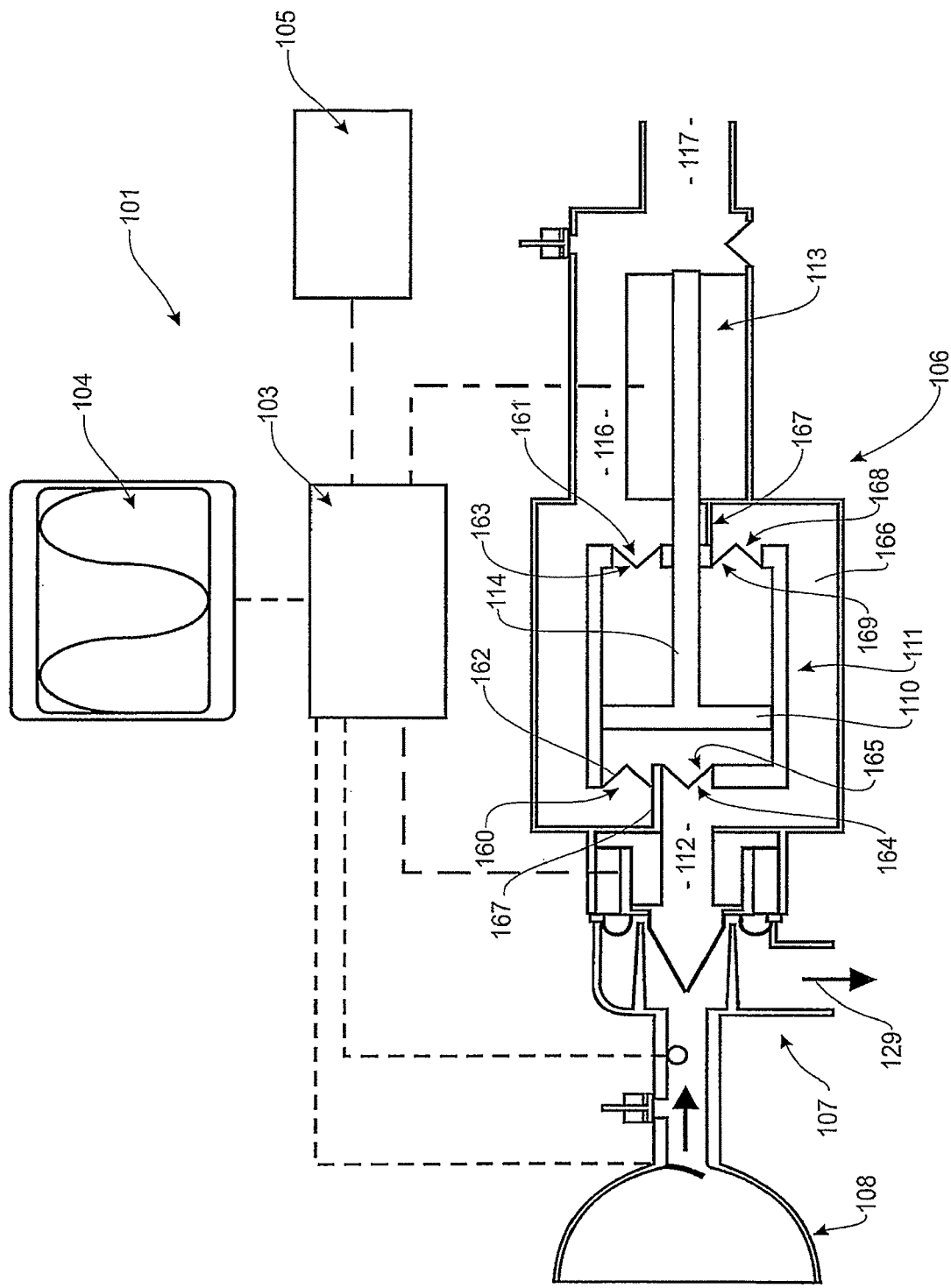
FIG. 5 is a schematic view of a variation of the resuscitator shown in an exhalation phase with reference to FIGS. 1-4.
Figure 8:
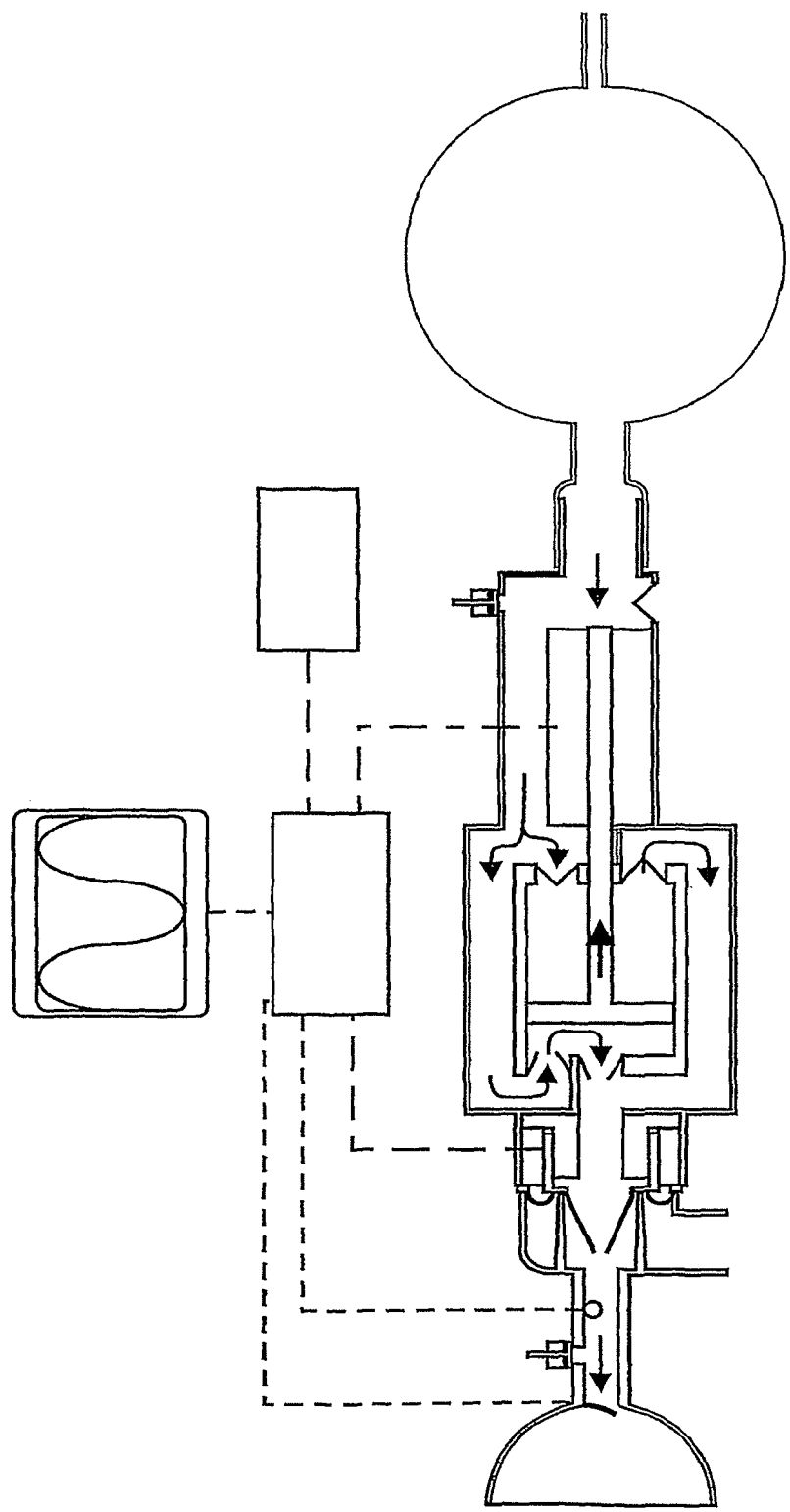
FIG. 8 shows the resuscitator of FIG. 5 in an inhalation mode and wherein an oxygen supply is provided to allow the operation of the resuscitator in a C-pap mode.
Figure 9:
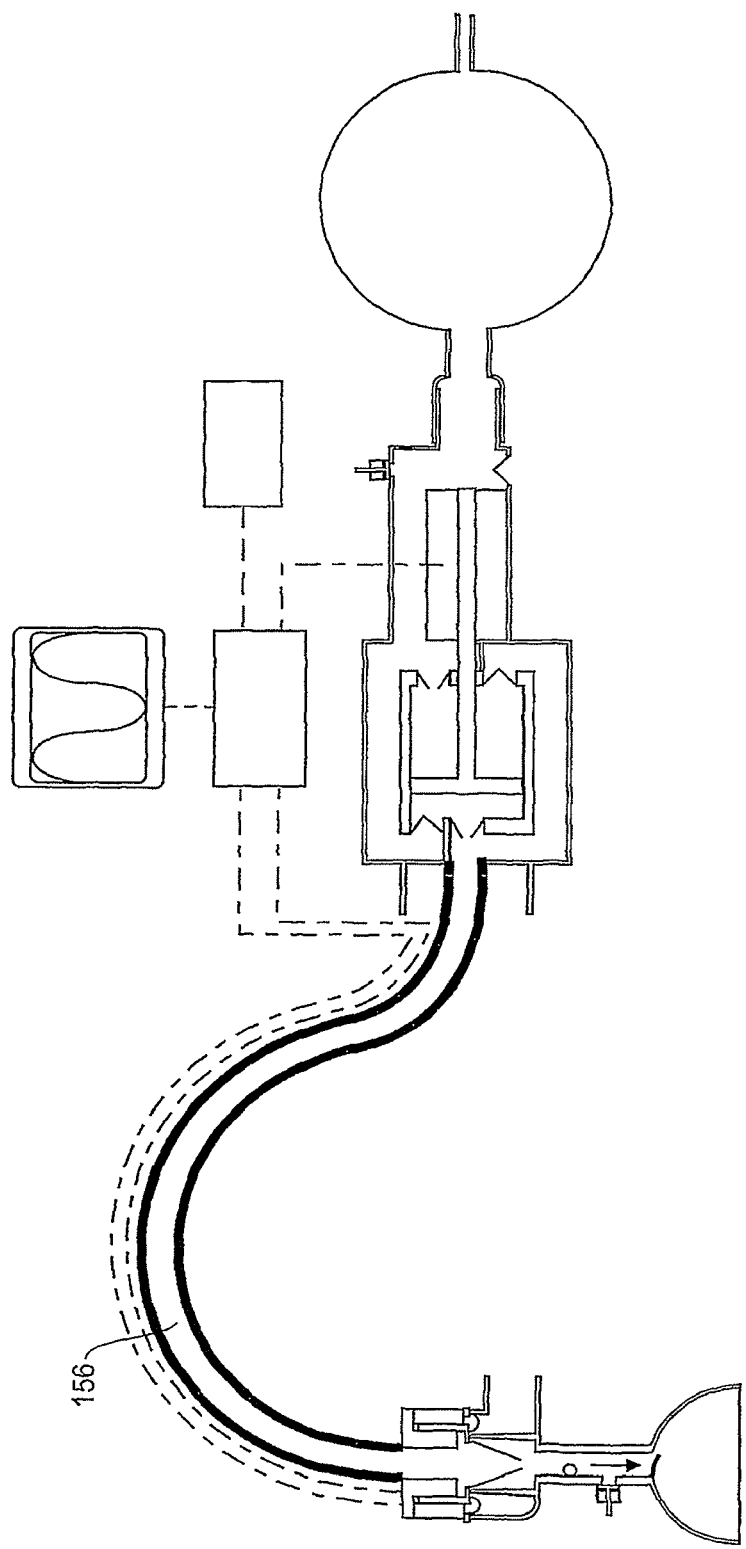
FIG. 9 illustrates the resuscitator of FIG. 5, wherein a flexible conduit is provided intermediate of certain parts of the resuscitator to provide, to a certain extent, independence of movement of the face mask relative to some of the other components of the resuscitator.

With reference to FIG. 8 the resuscitator described with reference to FIGS. 5-7 is also capable of operating in a supplementary gas and/or C-pap mode. This is shown for example in FIG. 8. Furthermore an extension conduit 156 may be utilised as shown in FIG. 9.

The number of oscillations that the piston may run through can be predetermined. The oscillations determine the tidal volume that is delivered to the patient. An operator may interact with the control unit and/or display to set parameters of operation of the resuscitator. Like the resuscitator described with reference to FIGS. 1-4 stroke length and position of the piston as well as airway pressures and tidal volume flow and volume sensing may occur and be recorded and displayed.

The airway pressure may be monitored by a pressure sensor. When the pressure sensor senses that the maximum predetermined airway pressure has been reached the controller then instructs the linear motor to stop or slow to maintain the maximum predetermined airway pressure for the duration of the inhalation period. Alternatively the controller may instruct the linear motor to stop to reduce pressure. In the event of any over pressure or system failure a safety valve like that described with reference to FIGS. 1-4 may open.

The voice coil actuator may be preloaded so that the exhaust port tends to an open biased condition allowing external air to enter the patient airway.

The resuscitator of FIGS. 5-9 may also operate in a PEEP mode as previously described. In the C-pap mode of operation all one-way valves to the cylinder are opened. This allows for direct transfer of gas from the inlet volute 116 to the outlet volute 166 and to the patient. Pressure sensors and relief valves may be included for failsafe purposes.

With reference to the resuscitators in FIGS. 1-9, parts of the resuscitator may be disposable. In particular those parts of the resuscitator that have been exposed to exhaled breath or air from a patient may be disposable. They may be manufactured and assembled in a way to facilitate their disposable use. For example the patient interface 8, the flow control unit 7 and one way valve 21 and/or the voice coil actuator 24, movable mouth 23 and housing 22 may all be disengageable from the pump unit 6 and be disposed after use. Circuits to allow for a quick connection of the controller 3 to a replacement assembly of such parts may be provided through simple plug/socket arrangement(s). A single plug/socket may be provided. This may automatically become coupled upon the engagement of the disposable components with the pump unit 6.

Figure 10:
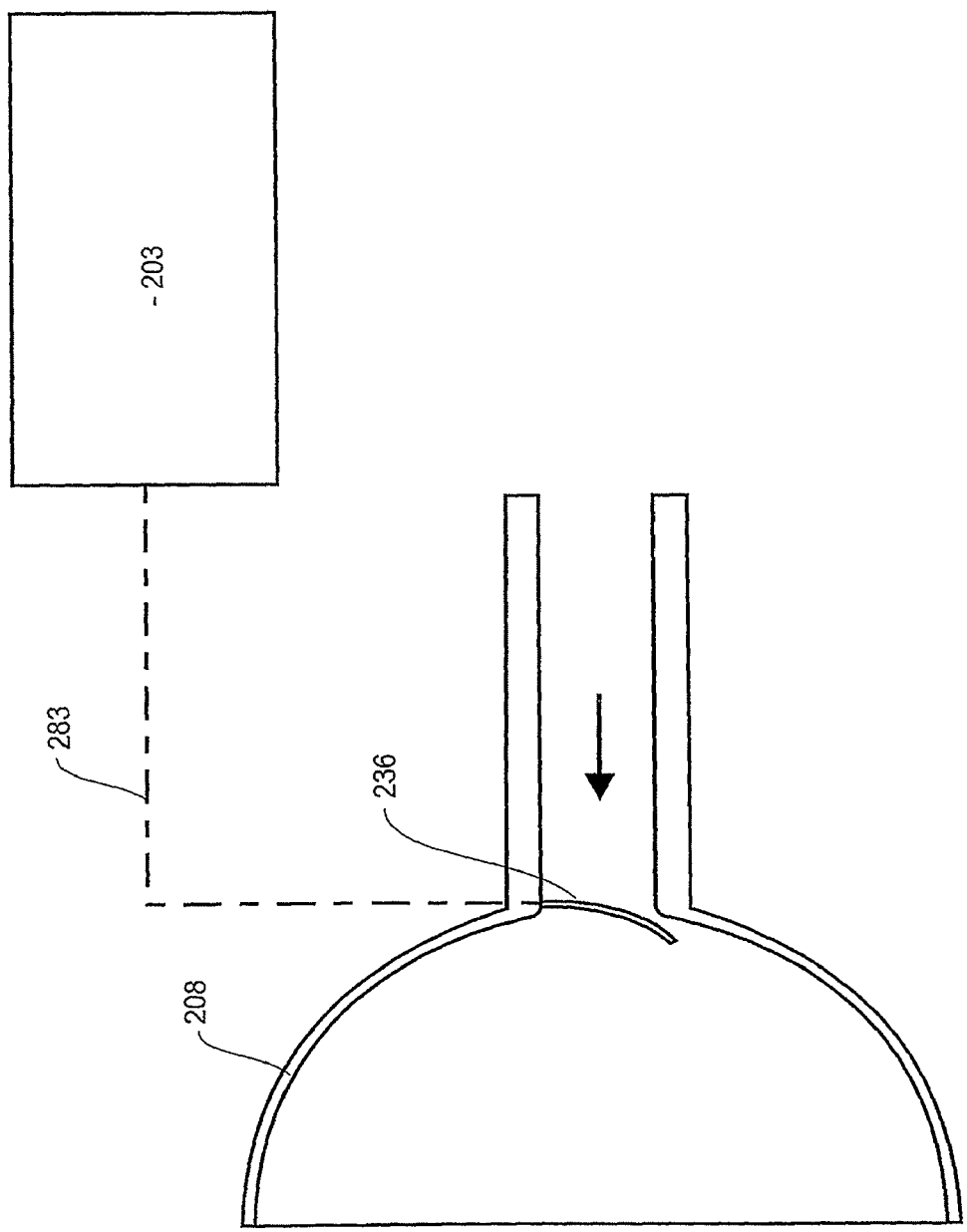
FIG. 10 is a sectional view of the face mask shown to include a flow and tidal volume sensor wherein the gas flow is shown in an inhalation direction.
Figure 11:
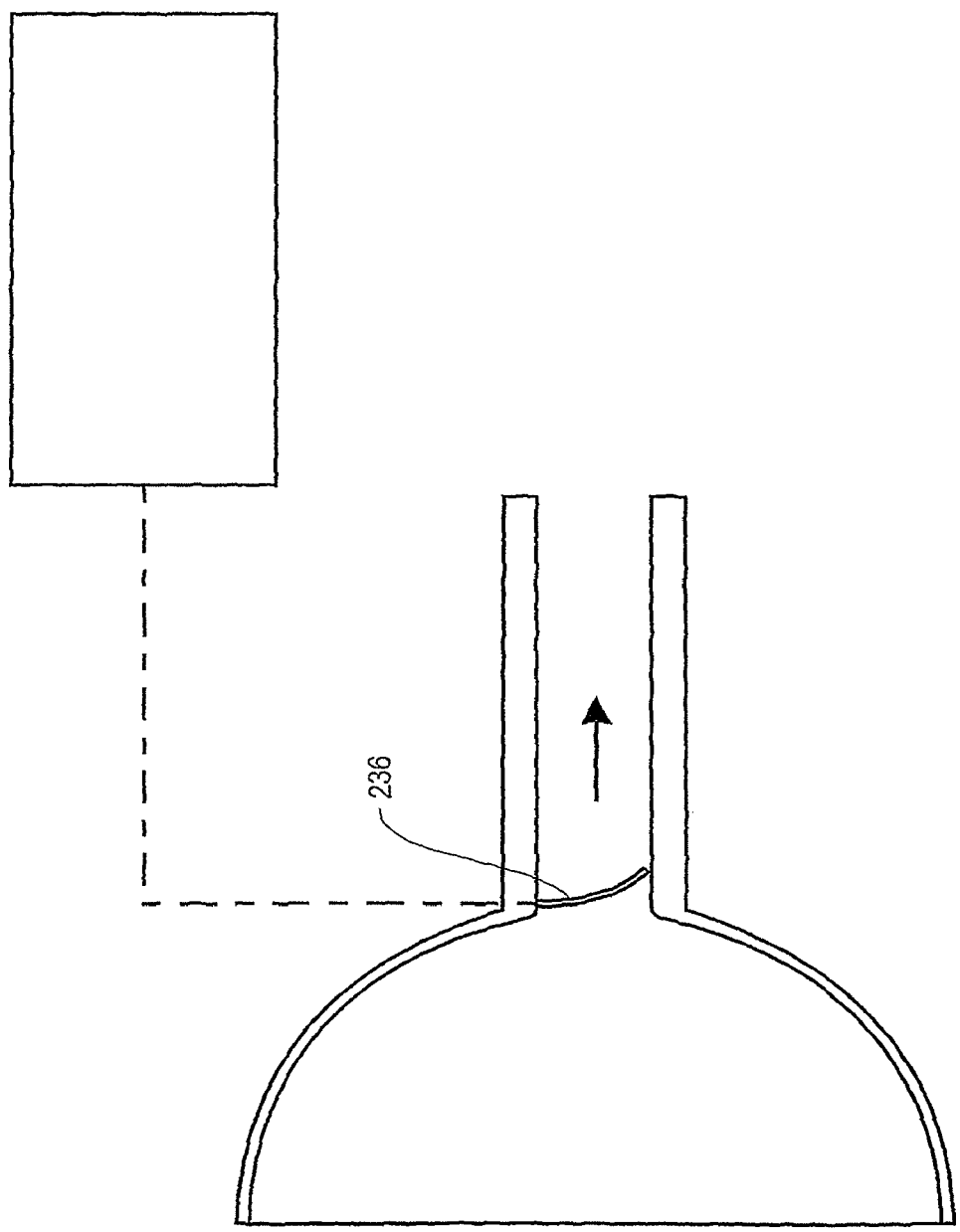
FIG. 11 is a variation to that shown in FIG. 10 wherein it is shown in an exhalation condition.

With reference to FIGS. 10 and 11 there is shown more detail in respect of the tidal volume and flow sensor. In FIG. 10 there is shown the patient interface 208 wherein the flow and tidal volume sensor 236 is shown during the inhalation phase of operation. It is connected to the controller 203 via a connection 283. With reference to FIG. 11, the sensor 236 is shown in the exhalation phase. The sensor 236 is of a kind that displaces dependent on air flow past it. Such may not be ideal for accurate sensing due to inertial mass of the sensor.

An alternative form of a sensor is one that has no inertial mass delay characteristics. An alternative form of sensor that may be used may be a gas flow meter that measure flow thermally. An example of such a flow meter is one manufactured by Sensirion.com such as their digital gas flow sensor ASF1400/ASF/1430. It may be one that is made in accordance to that described in U.S. Pat. No. 6,813,944. Such a flow sensor has a high response rate, given that it has unlike the sensor of FIG. 10, it has no mass to be displaced by the flow. A fast response can be beneficial. Such sensors may commonly be referred to as a hot wire flow sensor or thermal mass flow meters. The sensor or an alternative sensor may also measure the temperature of the exhaled breath. With an appropriate sensor where the response rate is very quick (a matter of, for example one tenths of a second) it is possible during the exhale of a patient to measure the patient's core temperature. This information may also be collected and/or displayed or otherwise used by the resuscitator.

The invention may offer the advantages of being portable, hand held (including being able to be held by one hand in order to hold the patient interface in the appropriate condition) and self contained by virtue of including its own power source (such as a 12 v power supply).

The device may have programmable profiles fixed and/or customised to suit patients, clinicians and operators requirements.

A heart rate monitoring facility may also be incorporated with the device, wherein heart rate can be accounted for in the control of the device and be displayed by the device.

The display can assist the operator in evaluating resuscitation of the patient. The performance, operating parameters and status of the features of the device are able to be recorded. This can assist in statistical analysis and to gather information for set-up of other devices.

The patient as herein defined may a mammal such a person or animal.

We claim:

1. A resuscitator for resuscitation of a patient, the resuscitator comprising:
   a) a pump including
   a rigid cylinder including at least one gas inlet and at least one gas outlet,
   a reciprocating piston movable to travel in said cylinder in a first stroke direction and an opposed second stroke direction, and
   at least one valve, the valve configured to allow gas to be displaced into said cylinder through said at least one gas inlet during at least one of a first stroke direction and/or a second stroke direction of said piston in said cylinder, and for allowing gas to be displaced through said at least one gas outlet during an opposite of said at least one of the first stroke direction and/or second stroke direction of said piston in said cylinder,
b) an accurately positionally controllable motor, operatively connected to said piston to move said piston in said cylinder, and
c) a controller configured for controlling the motor to control the position and displacement of the piston in the cylinder to provide a tidal volume of the gas for delivery to a patient at a pressure sufficient to inflate the lungs of the patient;
d) wherein the pump is engaged or engageable in ducted fluid connection with a patient interface for receiving gas via said at least one gas outlet and delivering said gas to said patient,
e) wherein intermediate of the patient interface and the at least one outlet of the cylinder and in said ducted fluid connection therewith is a gas flow controller the gas flow controller includes a one way valve that allows gas to be displaced from the outlet of the cylinder towards the patient interface and prevents gas from flowing through the one way valve in the opposite direction,
f) wherein one of the ducted fluid connection and the patient interface includes a pressure relief valve to allow pressure reduction of gas in said patient interface to occur, and
g) wherein said cylinder is split into two zones by said piston, a first zone being on one side of said piston and a second zone being on the other side of said piston and wherein said gas inlet(s) are provided to allow gas into the first zone and said gas outlet(s) are provided to allow gas out of said second zone, wherein a one way pump valve is provided to allow gas to transfer from said first zone to said second zone and that restricts flow in the opposite direction.

2. The resuscitator as claimed in claim 1 wherein the gas flow controller includes a valved exhaust port via which gas can exhaust to relieve pressure at the patient interface.

3. The resuscitator as claimed in claim 2 wherein said valved exhaust port assumes a closed condition when the piston is moving in a direction to displace gas towards the patient interface and assumes an open condition when the piston is moving in the opposite direction to allow gas due to exhalation of or by the patient to pass through the exhaust port.

4. The resuscitator as claimed in claim 3 wherein said valved exhaust port includes at least one opening closable by a valve, said valve mounted for movement relative the opening in a passive manner under the influence of pressure differential in the gas from controller and/or between the gas flow controller and ambient gas pressure.

5. The resuscitator as claimed in claim 4 wherein said valved exhaust port includes at least one opening closable by a valve, said valve mounted on or to or in operative association with an actuator to actively control the movement of the valve relative the opening.

6. The resuscitator as claimed in claim 3 wherein said valved exhaust port includes at least one opening closable by a valve, said valve mounted on or to or in operative association with an actuator to actively control the movement of the valve relative to the opening.

7. The resuscitator as claimed in claim 2 wherein said valved exhaust port is moved to a closed condition when gas is to be displaced into said patient and to an open condition to allow gas due to exhalation of or by the patient to pass through the exhaust port.

8. The resuscitator as claimed in claim 7 wherein said valved exhaust port includes at least one opening closable by a valve, said valve mounted for movement relative the opening in a passive manner under the influence of pressure differential in the gas from controller and/or between the gas flow controller and ambient gas pressure.

9. The resuscitator as claimed in claim 1 wherein said piston includes a connection rod with which said motor is in operative connection.

10. The resuscitator as claimed in claim 9 wherein said piston is or includes one part of a two moving part linear motor.

11. The resuscitator as claimed in claim 1 wherein said patient interface is a face mask or an endotracheal tube or naso-tube.

12. The resuscitator as claimed in claim 1 wherein the controller comprises a feedback system.

13. The resuscitator as claimed in claim 1 wherein said accurately positionally controllable motor is one or more selected from a stepper motor and a servo motor.

14. The resuscitator as claimed in claim 1 wherein said motor is a linearly operable motor.

15. The resuscitator as claimed in claim 1 wherein said motor is a linear stepper motor and is in part integrally formed with said piston.

16. The resuscitator as claimed in claim 1 wherein said motor is controlled by controller to ensure accurate velocity control of the motor.

17. The resuscitator as claimed in claim 1 wherein the motor is indirectly connected with said piston, via a linkage.

18. The resuscitator as claimed in claim 1 wherein the motor and cylinder are connected together.

19. A resuscitator for resuscitation of a patient, the resuscitator comprising:
a) a pump including
a rigid cylinder including at least one gas inlet and at least one gas outlet,
a reciprocating piston movable to travel in said cylinder in a first stroke direction and an opposed second stroke direction, and
at least one valve, the valve configured to allow gas to be displaced into said cylinder through said at least one gas inlet during at least one of a first stroke direction and/or a second stroke direction of said piston in said cylinder, and for allowing gas to be displaced through said at least one gas outlet during an opposite of said at least one of the first stroke direction and/or second stroke direction of said piston in said cylinder,
b) an accurately positionally controllable motor, operatively connected to said piston to move said piston in said cylinder, and
c) a controller configured for controlling the motor to control the position and displacement of the piston in the cylinder to provide a tidal volume of the gas for delivery to a patient at a pressure sufficient to inflate the lungs of the patient;
d) wherein the pump is engaged or engageable in ducted fluid connection with a patient interface for receiving gas via said at least one gas outlet and delivering said gas to said patient,
e) wherein intermediate of the patient interface and the at least one outlet of the cylinder and in said ducted fluid connection therewith is a gas flow controller the gas flow controller includes a one way valve that allows gas to be displaced from the outlet of the cylinder towards the patient interface and prevents gas from flowing through the one way valve in the opposite direction, f) wherein one of the ducted fluid connection and the patient interface includes a pressure relief valve to allow pressure reduction of gas in said patient interface to occur,
g) wherein said cylinder is split into two zones by said piston, a first zone being on one side of said piston and a second zone being on the other side of said piston, and
h) wherein the pump is a double acting pump that includes:
1) a first one way valve to
   i) allow gas to enter into the first zone via a first gas inlet of said cylinder during movement of the piston in said second stroke direction, and
   ii) restrict gas flow in the opposite direction through said first gas inlet during movement of the piston in the first stroke direction
2) a second one way valve to
   i) allow gas to exit the first zone via a first gas outlet of said cylinder during movement of the piston in its first stroke direction, and
   ii) restrict gas flow in the opposite direction through said first gas outlet during movement of the piston in the second stroke direction
3) a third one way valve to
   i) allow gas to enter into the second zone via a second gas inlet of said cylinder during movement of the piston in its first stroke direction, and
   ii) restrict gas flow in the opposite direction through said second gas inlet during movement of the piston in the second stroke direction
4) a fourth one way valve to
   i) allow gas to exit the second zone via a second gas outlet of said cylinder during movement of the piston in its second stroke direction, and
   ii) restrict gas flow in the opposite direction through said second gas outlet during movement of the piston in the first stroke direction; and
5) a manifold or ducting to duct gas from said first and second outlets to said patient interface.

* * * * *